United States Patent [19]

Lowey

[11] Patent Number: 4,680,323

[45] Date of Patent: Jul. 14, 1987

[54] METHOD AND COMPOSITION FOR THE PREPARATION OF CONTROLLED LONG-ACTING PHARMACEUTICALS FOR ORAL ADMINISTRATION

[76] Inventor: Hans Lowey, 1045 Nine Acres La., Mamaroneck, N.Y. 10543

[21] Appl. No.: 556,844

[22] Filed: Dec. 1, 1983

[51] Int. Cl.⁴ .................... A61K 9/22; A61K 9/26; C08L 1/26

[52] U.S. Cl. .................... 524/43; 514/781; 514/965; 424/435

[58] Field of Search .............. 424/19, 35, 20, 22; 514/781, 965; 524/43

[56] References Cited

U.S. PATENT DOCUMENTS

| | | | |
|---|---|---|---|
| 2,887,440 | 5/1959 | Greminger et al. | 514/781 |
| 3,065,143 | 11/1962 | Christenson et al. | 424/19 |
| 3,138,524 | 6/1964 | Zentner | 514/975 |
| 3,428,728 | 2/1969 | Lowey | 424/14 |
| 3,590,117 | 6/1971 | Christenson et al. | 424/19 |
| 3,870,790 | 3/1975 | Lowey et al. | 424/19 |
| 3,876,771 | 4/1975 | Denner | 514/781 |
| 4,226,849 | 10/1980 | Schor | 424/19 |
| 4,259,314 | 3/1981 | Lowey | 424/22 |
| 4,292,299 | 9/1981 | Suzuki et al. | 424/19 |
| 4,357,469 | 11/1982 | Schor | 536/91 |
| 4,369,172 | 1/1983 | Schor et al. | 514/781 |
| 4,389,393 | 6/1983 | Schor et al. | 514/781 |
| 4,540,566 | 9/1985 | Davis et al. | 424/22 |
| 4,572,832 | 2/1986 | Kigasawa et al. | 424/19 |

FOREIGN PATENT DOCUMENTS

| | | |
|---|---|---|
| 945899 | 4/1974 | Canada . |
| 1171691 | 11/1969 | United Kingdom . |
| 1279214 | 6/1972 | United Kingdom . |
| 1430684 | 3/1976 | United Kingdom . |
| 1583801 | 2/1981 | United Kingdom . |

*Primary Examiner*—Ronald W. Griffin
*Attorney, Agent, or Firm*—Curtis, Morris & Safford

[57] ABSTRACT

A novel pharmaceutical composition is disclosed. It comprises a sustained release pharmaceutical carrier suitable for admixture with active ingredients comprising:

(a) 5.5–98.5% by weight of hydroxypropyl methylcellulose;

(b) 0.25–4.5% by wieght of hydroxypropyl cellulose;

(c) 1–90% by weight of a carboxyvinyl polymer.

26 Claims, No Drawings

METHOD AND COMPOSITION FOR THE PREPARATION OF CONTROLLED LONG-ACTING PHARMACEUTICALS FOR ORAL ADMINISTRATION

This invention relates to a novel controlled long-acting dry pharmaceutical composition using a carrier or base material in admixture with an effective amount of a therapeutic agent or medicament. The unique composition of the base materials can be used for "one-a-day" controlled release tablets of zero order containing various medicaments. The sustained release composition can be formed into a lozenge, tablet or suppository. Because of its properties, the composition can also be used as a base composition in tablets for buccal administration.

BACKGROUND OF THE INVENTION

The advantages of long-acting or sustained release products are well-known. Such products are of great value in the pharmaceutical field because medication can be administered for uniform and continuous release over a prolonged period of time to achieve a stable and desired blood level of the active ingredient without requiring frequent administration of the medicament. The sustained release composition must meet certain criteria, namely it must provide uniform and constant dissolution and efficacy for a prolonged period of time, it must be easy to prepare, it must have acceptable taste and must be adaptable for use with a variety of therapeutic agents.

The use of cellulosic materials such as hydroxypropyl methylcellulose as an ingredient in pharmaceutical formulations is known. For example, U.S. Pat. No. 3,590,117 describes the use of hydroxypropyl methylcellulose in long-lasting troches used as vehicles for administering active medicaments. U.S. Pat. No. 3,870,790, describes mixing an active therapeutic ingredient with a copolymer of premoisturized hydroxypropyl methylcellulose powder optionally mixed with ethylcellulose powder. The release period of the active medicament is a function of the moisture content of the cellulose carrier.

In U.S. Pat. No. 4,259,314 there is described compositions which employ hydroxypropyl methylcellulose of different viscosity grades and hydroxypropyl cellulose in a dry powder composition which has particular value for use with hygroscopic active ingredients.

U.S. Pat. No. 4,292,299 to Suzuki et al. describes a long-acting buccal preparation which includes an adhesive outer layer comprising polymers which have adhesiveness to a wet mucous surface and which swell upon moistening together with a nonadhesive layer which is water soluble or water disintegrable. At least one of the layers is made to contain the active ingredient. The polymers suggested for use in the adhesive layer include homopolymers of acrylic acid monomers such as polyacrylic acid and related salts.

None of the compositions described in the prior art have demonstrated completely satisfactory properties for the administration of large active ingredient molecules. In particular the prior art compositions have not satisfactorily solved the problem of administering such molecules via desorption from the composition in the buccal pouch of the mouth. Nor have the prior art compositions demonstrated completely satisfactory characteristics where it is desired to administer active ingredients over a 12 to 24 hour time period.

OBJECTS OF THE INVENTION

It is accordingly an object of the invention to provide a controlled, long-acting pharmaceutical composition for effective administration of therapeutic agents.

It is another object of the invention to provide a new base material or carrier which can be used in admixture with a variety of therapeutic agents and which can also be easily and inexpensively manufactured.

It is a further object to provide a method for producing a controlled, long-acting pharmaceutical composition which can be used for administering large active ingredient molecules.

It is still a further object of the invention to provide a method and composition for preparing a sustained release pharmaceutical formulation which can be used to administer large molecules of active ingredient via the buccal pouch of the mouth.

It is yet a further object of the invention to provide a method and composition for preparing a sustained release pharmaceutical formulation which can be used to administer active ingredients over a 12 to 24 hour time frame, i.e., a so-called "zero order" sustained release composition.

Other objects of the invention will be apparent from the following discussion.

GENERAL DESCRIPTION

These and other objects of the invention are achieved by using a carrier prepared from at least three components. Broadly, the carrier is comprised of:
(a) 5.5–98.5% by weight of hydroxypropyl methylcellulose;
(b) 0.25–4.5% by weight of hydroxypropyl cellulose; and
(c) 1–90% by weight of a carboxyvinyl polymer.
Desirably, the carrier is comprised of:
(a) 10–80% by weight of hydroxypropyl methylcellulose;
(b) 1.0–3.5% by weight of hydroxypropyl cellulose; and
(c) 3–75% by weight of a carboxyvinyl polymer.
In preferred form the carrier is comprised of:
(a) 2–35% by weight of hydroxypropyl methylcellulose having a viscosity of about 50 centipoise for a 2% aqueous solution at 20° C.;
(b) 3–85% by weight of hydroxypropyl methylcellulose having a viscosity of about 4,000 centipoise for a 2% aqueous solution at 20° C.; and
(c) 2–40% by weight of hydroxypropyl methylcellulose having a viscosity of about 15,000 centipoise for a 2% aqueous solution at 20° C.;
(d) 0.5–40% by weight of hydroxpropyl methylcellulose having a viscosity of about 100,000 centipoise for a 2% aqueous solution at 20° C.;
(e) 0.25 to 4.5% by weight of hydroxypropyl cellulose; and
(f) 1 to 90% of a carboxyvinyl polymer having a viscosity of 30,000 to 40,000 centipoise for a 3.0% by weight neutralized solution.

Preferably the hydroxypropyl cellulose which is used has a viscosity of 1000 to 4500 when measured as a 2% by weight aqueous solution.

Hydroxypropyl methylcellulose having viscosities of 50 and 4000 centipoise for 2% aqueous solutions at 20° C. are known and commercially available as Methocel E-50 and E-4M, respectively (Dow Chemical Company registered trademarks). Hydroxypropyl methylcellulose having viscosities of 15,000 and 100,000 centipoise for 2% aqueous solutions at 20° C. are known and commercially available as Methocel K-15M and K-100M, respectively (Dow Chemical Company registered trademarks). Hydroxypropyl cellulose as used in accordance with the invention is known and commercially available as Klucel (a Hercules Inc. registered trademark).

The carboxyvinyl polymers used in the invention are acrylic acid polymers cross linked with a polyalkenyl polyether. The polymers are available from the B. F. Goodrich Company under the trademark Carbopol. They have viscosities of 30,000–40,000 centipoise for 3% aqueous solutions. The polymer is a weak acid and reacts to form salts. Therein lies their efficacy in providing a zero order release rate under the alkaline conditions found in the small intestine.

The mixtures of hydroxypropyl methylcellulose, hydroxypropyl cellulose and polyacrylic acid are prepared in a straightforward method. The several components are added in the desired proportions to one another and thoroughly mixed to form a uniform composition. Thereafter from 2 to 700 mg of an active ingredient are added to the carrier and the pharmaceutical composition is compressed and shaped into a convenient pharmaceutical form. Depending upon the conditions under which the material is compressed and further depending on the relative proportions of the several components, one obtains a product of unique sustained release characteristic. The sustained release characteristic of the composition can be predetermined and varied by adjusting the makeup of the composition within the aforesaid limits and/or by adjusting the compression of the tablet.

If the pharmaceutical composition is compressed under low pressure, a troche or buccal tablet can be prepared capable of being sucked or used in the mouth. A controlled release of the active therapeutic agent which is mucosally absorbed into the blood stream is achieved. If higher pressures are used to compress the pharmaceutical material a harder and longer-lasting pharmaceutical composition can be prepared suitable for rectal or vaginal application or suitable for swallowing in the form of a tablet. The final products may additionally contain adjuvants such as coloring agents, flavoring agents, synthetic sweetening agents and preservatives.

To make the absorption of large molecules through the buccal pouch possible, a sweetening agent like saccharin, cyclamate, Aspartame, or any other chemical which is at least 30 times as sweet as sugar is added to the base material in a quantity of 2 mg or more.

The pharmaceutical compositions obtained using the dry carrier base material of the invention have controlled, long-acting capability so that therapeutically active agents can be uniformly and continuously released over prolonged periods of time ranging from about 2 to 24, or more, hours. The duration, uniformity and continuity of release of the therapeutically active ingredient can be suitably controlled by varying the relative amounts of hydroxypropyl methylcellulose, hydroxypropyl cellulose and carboxyvinyl polymer and/or by changing the surface of the finished product. The dry pharmaceutical formulation of the invention has considerable flexibility and versatility depending upon the form in which it is administered and the particular nature of the active therapeutic agent combined with the dry carrier base material.

EXAMPLES

In each of the following examples the carrier composition defined was prepared by mixing the several components in the desired proportion in a mixing bowl. The mixture was thoroughly stirred to achieved uniformity and thereafter the desired amount of active ingredient and other adjuvants were added in the amounts indicated.

The carrier, excipients and active ingredients were then thoroughly mixed and thereafter compressed into tablets at a compression of from 6 to 10 kg./cm$^2$.

EXAMPLE I

|  | Weight | Base Composition in Percent |
|---|---|---|
| Pseudephedrine HCl | 120 mg |  |
| E-4M | 55 mg | 73.3333% |
| K-15M | 15 mg | 20.0000% |
| Klucel | 3 mg | 4.0000% |
| Carbopol | 2 mg | 2.6667% |

EXAMPLE II

| | Weight | Base Composition in Percent |
|---|---|---|
| Hexocyclium methylsulfate | 50 mg | |
| E-4M | 42.5 mg | |
| K-15M | 5.0 mg | 98.5% |
| K-100M | 1.75 mg | |
| Carbopol | .5 mg | 1.0% |
| Klucel | .25 mg | 0.5% |

EXAMPLE III

| | Weight | Base Composition in Percent |
|---|---|---|
| Procainamide HCL | 250 mg | |
| E-50 | 12.5 mg | 9.6525% |
| E-4M | 80 mg | 61.7761% |
| K-15M | 30 mg | 23.1660% |
| Carbopol | 5 mg | 3.8610% |
| Klucel | 2 mg | 1.5444% |

EXAMPLE IV

| | Weight | Base Composition in Percent |
|---|---|---|
| Ethaverine HCL | 150 mg | |
| K-15M | 6.75 mg | 4.5% |
| K-100M | 1.5 mg | 1.0% |
| Carbopol | 135 mg | 90.0% |
| Klucel | 6.75 mg | 4.5% |

EXAMPLE V

| | Weight | Base Composition in Percent |
|---|---|---|
| Imipramine HCL | 50 mg | |
| E-4M | 30 mg | 52.6316% |
| K-100M | 15 mg | 26.3158% |
| Carbopol | 10 mg | 17.5438% |
| Klucel | 2 mg | 3.5088% |

EXAMPLE VI

| | Weight | Base Composition in Percent |
|---|---|---|
| Ferrous fumarate | 320 mg | |
| K-15M | 120 mg | 69.3641% |
| K-100M | 25 mg | 14.4509% |
| Klucel | 3 mg | 1.7341% |
| Carbopol | 25 mg | 14.4509% |

EXAMPLE VII

| | Weight | Base Composition in Percent |
|---|---|---|
| Dextrometorphan HBR (lozenge) | 15 mg | |
| E-4M | 13.5 mg | 3.8849% |
| Mannitol | 320 mg | 92.0863% |
| Hexanitrate | | |
| Carbopol | 13.5 mg | 3.8849% |
| Klucel | 0.5 mg | 0.1439% |

EXAMPLE VIII

| | Weight | Base Composition in Percent |
|---|---|---|
| Hydralazine HCL | 100 mg | |
| E-4M | 75 mg | 72.1154% |
| K-100M | 20 mg | 19.2308% |
| Klucel | 4 mg | 3.8461% |
| Carbopol | 5 mg | 4.8077% |

EXAMPLE IX

| | Weight | Base Composition in Percent |
|---|---|---|
| Indomethacin | 75 mg | |
| E-4M | 40 mg | 53.33% |
| K-15M | 25 mg | 33.33% |
| Klucel | 3 mg | 4.00% |
| Carbopol | 7 mg | 9.33% |

EXAMPLE X

| | Weight | Base Composition in Percent |
|---|---|---|
| Meprobamate | 400 mg | |
| E-50 | 70 mg | 34.3137% |
| K-15M | 80 mg | 39.2157% |
| K-100M | 30 mg | 14.7059% |
| Carbopol | 20 mg | 9.8039% |
| Klucel | 4 mg | 1.9608% |

EXAMPLE XI

| | Weight | Base Composition in Percent |
|---|---|---|
| Secobarbital sodium (suppositories) | 200 mg | |
| K-15M | 130 mg | 19.9386% |
| K-100M | 80 mg | 12.2700% |
| Carbopol | 40 mg | 6.1350% |
| Klucel | 2 mg | .3067% |
| Excipients | 400 mg | 61.3497% |

EXAMPLE XII

| | Weight | Base Composition in Percent |
|---|---|---|
| Phenylpropanolamine | 75 mg | |
| E-4M | 30 mg | 38.4615% |
| K-15M | 20 mg | 25.6410% |
| K-100M | 10 mg | 12.8205% |
| Carbopol | 15 mg | 19.2308% |
| Klucel | 3 mg | 3.8462% |

The novel carriers of the invention can be used with a wide variety of active therapeutic agents. The improved long acting compositions can be used, without limitation, as cardiovasculars, anti-inflammatories, analgesics, antiarrhymetics, bronchodilators, tranquilizers, calcium blockers, beta-blockers, decongestants, antispasmodics, weight control, antacids, cold and allergy products, and sedatives. It will be well understood by those skilled in the art that certain equivalents of each as shown may be employed and it will be recognized that various modifications are possible within the scope of the invention as defined in the following claims.

What is claimed is:

1. A sustained release pharmaceutical carrier suitable for admixture with active ingredients comprising:
   (a) 5.5-98.5% by weight of hydroxypropyl methylcellulose;
   (b) 0.25-4.5% by weight of hydroxypropyl cellulose;
   (c) 1-90% by weight of a carboxyvinyl polymer.

2. A sustained release pharmaceutical carrier as defined in claim 1 wherein the hydroxypropyl cellulose has a viscosity in the range of 1,000 to 1,500 centipoise for a 2% aqueous solution at 25° C.

3. A sustained release pharmaceutical carrier as defined in claim 1 adapted for facilitating the absorption of large molecules through the buccal pouch of the mouth containing a sweetening agent at least 30 times as sweet as sugar.

4. A sustained release pharmaceutical carrier according to claim 1, wherein the carboxyvinyl polymer is a polymer of acrylic acid or polyacrylic acid, cross-linked with a polyalkenyl polyether.

5. A sustained release pharmaceutical carrier suitable for admixture with active ingredients comprising:
   (a) 10-80% by weight of hydroxypropyl methylcellulose;
   (b) 1.0-3.5% by weight of hydroxypropyl cellulose;
   (c) 3-75% by weight of a carboxyvinyl polymer.

6. A sustained release pharmaceutical carrier according to claim 5, wherein the carboxyvinyl polymer is a polymer of acrylic acid or polyacrylic acid, cross-linked with a polyalkenyl polyether.

7. A sustained release pharmaceutical carrier suitable for admixture with active ingredients and particularly adapted for preparation of compositions suitable for administration of active ingredients through the buccal pouch of the mouth which comprises:
   (a) 2-35% by weight of hydroxypropyl methylcellulose having a viscosity of about 50 centipoise for a 2% aqueous solution at 20° C.;
   (b) 3-85% by weight of hydroxypropyl methylcellulose having a viscosity of about 4,000 centipoise for a 2% aqueous solution at 20° C.; and
   (c) 2-40% by weight of hydroxypropyl methylcellulose having a viscosity of about 15,000 centipoise for a 2% aqueous solution at 20° C.;
   (d) 0.5-40% by weight of hydroxpropyl methylcellulose having a viscosity of about 100,000 centipoise for a 2% aqueous solution at 20° C.;
   (e) 0.25-4.5% by weight of hydroxypropyl cellulose; and (f) 1–90% of a carboxyvinyl polymer having a viscosity of 30,000 to 40,000 centipoise for a 3.0% by weight neutralized solution.

8. A sustained release pharmaceutical carrier as defined in claim 7 wherein the hydroxypropyl cellulose has a viscosity in the range of 1,000 to 1,500 centipoise for a 2% aqueous solution at 25° C.

9. A sustained release pharmaceutical carrier according to claim 7, wherein the carboxyvinyl polymer is a polymer of acrylic acid or polyacrylic acid, cross-linked with a polyalkenyl polyether.

10. A sustained release pharmaceutical composition which comprises a carrier and an active therapeutic agent incorporated within said carrier, said carrier comprising:
(a) 5.5–98.5% by weight of hydroxypropyl methylcellulose;
(b) 0.25–4.5% by weight of hydroxypropyl cellulose;
(c) 1–90% by weight of a carboxyvinyl polymer.

11. A sustained release pharmaceutical carrier as defined in claim 10 adapted for facilitating the absorption of large molecules through the buccal pouch of the mouth containing a sweetening agent at least 30 times as sweet as sugar.

12. A sustained release pharmaceutical composition as defined in claim 11 wherein said therapeutic agent is present in an amount of 0.25 to 700 mg.

13. A sustained release pharmaceutical composition as defined in claim 11 wherein the hydroxypropyl cellulose has a viscosity of 1,000 to 1,500 for a 2% aqueous solution at 25° C.

14. A sustained release pharmaceutical carrier as defined in claim 10 which is zero order with respect to its release of active ingredient.

15. A sustained release pharmaceutical carrier as defined in claim 10 which is adapted for use in a one-a-day tablet.

16. A sustained release pharmaceutical composition as defined in claim 10 wherein the said therapeutic agent is present in from 0.25 to 700 mg.

17. A sustained release pharmaceutical composition as defined in claim 10 wherein the carrier contains hydroxypropyl cellulose having a viscosity of 1,000 to 1,500 centipoise for a 2% aqueous solution at 25° C.

18. A sustained release pharmaceutical composition according to claim 10, wherein the carboxyvinyl polymer is a polymer of acrylic acid or polyacrylic acid, cross-linked with a polyalkenyl polyether.

19. A sustained release pharmaceutical composition which comprises a carrier and an active therapeutic agent incorporated within said carrier, said carrier comprising:
(a) 10–80% by weight of hydroxypropyl methylcellulose;
(b) 1.0–3.5% by weight of hydroxypropyl cellulose; and
(c) 3–75% by weight of a carboxyvinyl polymer.

20. A sustained release pharmaceutical composition according to claim 19, wherein the carboxyvinyl polymer is a polymer of acrylic acid or polyacrylic acid, cross-linked with a polyalkenyl polyether.

21. A sustained release pharmaceutical composition adapted for administration via the buccal pouch of the mouth which comprises a sustained release carrier and an active therapeutic agent, said carrier comprising:
(a) 2–35% by weight of hydroxypropyl methylcellulose having a viscosity of about 50 centipoise for a 2% aqueous solution at 20° C.;
(b) 3–85% by weight of hydroxypropyl methylcellulose having a viscosity of about 4,000 centipoise for a 2% aqueous solution at 20° C.; and
(c) 2–40% by weight of hydroxypropyl methylcellulose having a viscosity of about 15,000 centipoise for a 2% aqueous solution at 20° C.;
(d) 0.5–40% by weight of hydroxypropyl methylcellulose having a viscosity of about 100,000 centipoise for a 2% aqueous solution at 20° C.;
(e) 0.25–4.5% by weight of hydroxypropyl cellulose; and
(f) 1–90% of a carboxyvinyl polymer having a viscosity of 30,000 to 40,000 centipoise for a 3.0% by weight neutralized solution.

22. A sustained release pharmaceutical composition according to claim 21, wherein the carboxyvinyl polymer is a polymer of acrylic acid or polyacrylic acid, cross-linked with a polyalkenyl polyether.

23. A method for producing a sustained zero-order time release of an active pharmaceutical agent in the gastro-intestinal tract comprising:
forming an ingestible tablet containing a carrier of hydroxypropyl methylcellulose, hydroxypropyl cellulose and a carboxy vinyl polymer, together with an effective amount of a pharmaceutically active agent;
ingesting the tablet; and
allowing the tablet to transit the gastro-intestinal tract and to slowly dissolve by the action of gastro-intestinal fluids thereupon, whereby the weakly acidic carboxy vinyl polymer reacts to form salts under the alkaline conditions in the small intestine of the gastro-intestinal tract to thereby produce a coating of the active pharmaceutical agent on the small intestine of the gastro-intestinal tract, which coating remains in place and from which the pharmaceutically active agent is slowly absorbed through the mucosa of the small intestine into the blood stream over a sustained period of from twelve to twenty-four hours, which is in excess of the time taken by an undissolved remnant of the tablet to transit the gastro-intestinal tract.

24. A method for producing a sustained zero-order time release of an active pharmaceutical agent in the gastro-intestinal tract utilizing an ingestible tablet prepared according to claim 23, wherein the carboxyvinyl polymer is a polymer of acrylic acid or polyacrylic acid, cross-linked with a polyalkenyl polyether.

25. A method for facilitating the sustained time-release and absorption of large molecules of a pharmaceutically active agent through the mucosa of the buccal pouch of the mouth comprising:
forming a buccal tablet containing a carrier of hydroxypropyl methylcellulose, hydroxypropyl cellulose and a carboxy vinyl polymer, together with an effective amount of a pharmaceutically active agent having a molecule size larger than the normal permeability of the mucosa in the buccal pouch of the mouth, and a sweetening agent at least thirty times as sweet as sugar;
placing the buccal tablet in the buccal pouch of the mouth; and
allowing saliva in the buccal pouch of the mouth to slowly dissolve the tablet such that the sweetener contacts the mucosa lining the buccal pouch of the mouth and causes an increase in the permeability of the mucosa to allow the molecules of the pharmaceutically active agent to penetrate and be absorbed into the bloodstream over a sustained period.

26. A method for facilitating the sustained time-release and absorption of large molecules of a pharmaceutically active agent through the mucosa of the buccal pouch of the mouth, utilizing a buccal tablet prepared according to claim 25, wherein the carboxyvinyl polymer is a polymer of acrylic acid or polyacrylic acid, cross-linked with a polyalkenyl polyether.

* * * * *